United States Patent [19]

Lybrand et al.

[11] 4,004,002
[45] Jan. 18, 1977

[54] ANTI-INFLAMMATORY AGENTS COPRECIPITATED WITH LIGNO-SULFONIC ACID

[75] Inventors: Robert Archie Lybrand, Ashland; Louis Gary Bell, Richmond, both of Va.

[73] Assignee: A. H. Robins Company, Incorporated, Richmond, Va.

[22] Filed: Nov. 3, 1975

[21] Appl. No.: 628,258

Related U.S. Application Data

[63] Continuation-in-part of Ser. No. 459,828, April 10, 1974, abandoned, which is a continuation-in-part of Ser. Nos. 271,986, July 14, 1972, abandoned, and Ser. No. 89,999, Nov. 16, 1970, abandoned.

[52] U.S. Cl. .............................. 424/230; 424/180; 424/273; 424/274
[51] Int. Cl.$^2$ ........................................ A61K 31/60
[58] Field of Search ........... 424/180, 273, 274, 230

[56] References Cited

UNITED STATES PATENTS 2,838,483   6/1958   Jantzen .............................. 260/124

OTHER PUBLICATIONS

Barr et al. O–T–C Internal Analgesics Handbook of Non–Prescription Drugs, pp. 26–36 (1967).
Chemical Abstracts 51:18295i (1957).
Chemical Abstracts 69:94870h (1968).
Kirk–Othmer–Encyclopedia of Chem. Tech. pp. 369–381, vol. 12, (1967).

Primary Examiner—Leonard Schenkman

[57] ABSTRACT

Coprecipitates of anti-inflammatory agents and ligno-sulfonic acid which retain the therapeutic activity of the anti-inflammatory agent and which prevent irritation of the gastric mucosa are disclosed. The method of preparing the coprecipitates is described.

19 Claims, No Drawings

ANTI-INFLAMMATORY AGENTS COPRECIPITATED WITH LIGNO-SULFONIC ACID

This application is a continuation-in-part application of copending application Ser. No. 459,828 filed Apr. 10, 1974 now abandoned, which is a continuation-in-part application of copending applications Ser. No. 271,986 filed July 14, 1972, and Ser. No. 89,999 filed Nov. 16, 1970, both now abandoned.

The present invention relates to anti-inflammatory agents and is more particularly concerned with certain coprecipitates of lignosulfonic acids and anti-inflammatory agents such as aspirin, phenylbutazone and indomethacin which possess a high degree of anti-inflammatory activity and which prevent gastric irritation, therapeutic compositions containing said coprecipitates as active ingredients and methods for the preparation and use of said coprecipitates.

It has long been known that orally administered anti-inflammatory drugs such as aspirin often cause gastric irritation and in some instances bleeding and ulceration. Undispersed particles of tableted drugs may lodge in the folds of the stomach tissue or agglomerates of the drugs which generally have low solubility may adhere to the surface of tissue or there may be insufficient liquids to suspend the drugs. These conditions may lead quickly to gastric lesions and bleeding. The drugs may be particularly damaging to individuals who require large dosages and treatment for extended periods of time. Attempts to reduce gastric irritation have been made by combining aspirin with aluminum and magnesium adjuncts or other buffering materials and the efficacy of such combinations has not been fully determined and is still the subject of medical debate. Reduced gastric irritation has been reported using aspirin-caseinate by Feinblatt, T. M. and Ferguson, E. Q. "Aspirin-Caseinate in Patients With Gastric Sensitivity to Plain Aspirin," New York State Journal of Medicine, Vol. 63 (19), Oct. 1, 1963, p. 2805–2807.

The present invention is based on the discovery that coprecipitates of lignosulfonic acids and anti-inflammatory agents such as aspirin, phenylbutazone and indomethacin can be readily prepared, that the therapeutic activity of the anti-inflammatory agents has not been diminished and that said coprecipitates are especially effective in preventing gastric irritation and bleeding of the gastric mucosa.

It is, therefore, a primary object of the present invention to provide coprecipitates of lignosulfonic acids and anti-inflammatory agents. A further object is to provide coprecipitates of lignosulfonic acids and anti-inflammatory agents useful for the alleviation of distress caused by inflamed tissue. A still further object is to provide coprecipitates of lignosulfonic acids and anti-inflammatory agents useful for the alleviation of distress caused by inflamed tissue and having minimal side effects. Another object is to provide methods whereby coprecipitates of lignosulfonic acids and anti-inflammatory agents useful in the treatment of inflamed tissue can readily be prepared. Other objects will be readily apparent to one skilled in the art, and still other objects will become apparent hereinafter.

The foregoing and additional objects are accomplished by the provision of coprecipitates of lignosulfonic acids and anti-inflammatory agents such as aspirin, phenylbutazone and indomethacin. The coprecipitates are of particular interest in that they retain the valuable therapeutic activity of the anti-inflammatory agent coupled with a very low degree of side effects upon administration. The lignosulfonic acid portion of the coprecipitate varies from 3 to 10 weight %. The aspirin, phenylbutazone or indomethacin portion of the coprecipitate varies from 90 to 97 weight %.

The novel coprecipitates of the present invention are distinguishable from simple mixtures of lignosulfonic acids and anti-inflammatory agents by the water insolubility of the coprecipitates, whereas the washing of simple mixtures of lignosulfonic acids and anti-inflammatory agents results in solution of the lignosulfonic acid portion of the mixture.

Indicative of the bound nature of the contained lignosulfonic acids in the coprecipitates of this invention is the change to water insolubility and non-leaching characteristic of said contained lignosulfonic acids. Specifically, this may be demonstrated by slurrying coprecipitates with water and washing with water on a suction funnel and comparing leachability with that of thoroughly triturated mixtures. Typical results are as follows:

|  | Weight % Contained Lignosulfonic Acid Before Leaching | Ratio Wash Water to Solid | Weight % Lignosulfonic In Insoluble Portion After Washing |
|---|---|---|---|
| Lignosulfonic Acid-Aspirin Coprecipitate | 5.0 | 10 to 1 | 5.0 |
| Lignosulfonic Acid-Aspirin Mixture | 5.0 | 10 to 1 | 0.1 |
| Lignosulfonic Acid-Phenylbutazone Coprecipitate | 3.8 | 100 to 1 | 3.1 |
| Lignosulfonic Acid-Phenylbutazone Mixture | 5.0 | 100 to 1 | 0.2 |

When the anti-inflammatory agents are dissolved away from the coprecipitates with chloroform, the lignosulfonic acid residues account for substantially all the lignosulfonic acid contained originally in the coprecipitates and are now readily soluble in water.

The term "lignosulfonic acid" refers to a material generally available from the sulfite, sulfate, soda-ammonia base and other conventional processes for pulping wood. "Lignosulfonate" refers to a salt of lignosulfonic acid. Lignosulfonic acids are available in a variety of forms generally in the form of a salt or mixture of salts thereof, and unless otherwise specifically used or described herein the term lignosulfonic acid is intended to include the free acid and any salt havig the desired properties and activities of the acid base. Thus, both the free lignosulfonic acids and salts thereof are within the scope of the present invention.

The ammonium lignosulfonate and the sodium lignosulfonate used in preparing the novel coprecipitates of the present invention are sold by the Arthur Trask Co. of Chicago, Ill., under the trade names of Peritan[TM]. The materials are prepared by processes essentially described in U.S. Pat. No. 2,838,483. A typical analysis of ammonium Peritan is as follows:

| PERITAN NH$_4$[TM] (Ammonium Lignosulfonate) | | |
|---|---|---|
| Total Solids (15 hrs. at 103° C.) | | 92.63% |
| Moisture Content (Fischer) | | 6.59% |
| Water Insolubles | | 0.10% |
| pH (1% Solution) | | 5.80 |
| Density (lbs/cubic ft.) | | 35.83 |
| Ammonium Lignosulfonate (UV absorption method) | | 90.00% |
| High Molecular Weight | 34.8% | |
| Low Molecular Weight | 65.2% | |
| | Per Cent of Total Solids | |
| Reducing Sugars (as glucose) | | 0.20 |
| Total Sulfur (S) | | 7.02 |
| Titratable SO$_2$ | | 0.62 |
| Organically Combined SO$_2$ | | 2.59 |
| Methoxyl | | 11.42 |
| Carbon (C) | | 53.20 |
| Hydrogen (H) | | 6.40 |
| Total Nitrogen (as NH$_3$) | | 3.68 |
| NH$_3$ plus (as NH$_3$) | | 3.55 |
| Organically Combined Nitrogen (as NH$_3$) | | 0.13 |
| Sulfated Ash | | 2.16 |
| Na$_2$SO$_4$ | 12.80% of sulfated ash | |
| CaSO$_4$ | 83.50% of sulfated ash | |
| Cr$_2$O$_3$ | 0.91% of sulfated ash | |
| Fe$_2$O$_3$ | 0.16% of sulfated ash | |

A typical analysis of Sodium Peritan is as follows:

| PERITAN Na[TM] (Sodium Lignosulfonate) | | |
|---|---|---|
| Total Solids (15 hours at 103° C.) | | 92.70% |
| Moisture Content (Fischer) | | 7.23% |
| Water Insolubles | | 0.10% |
| pH (1% solution) | | 8.84 |
| Density (lbs/cubic ft.) | | 38.58 |
| Sodium Lignosulfonate (UV absorption method) | | 90.0 |
| High Molecular Weight | 39.0% | |
| Low Molecular Weight | 61.0% | |
| | Per Cent of Total Solids | |
| Reducing Sugars (as glucose) | | 0.14 |
| Total Sulfur (S) | | 6.67 |
| Titratable SO$_2$ | | 0.75 |
| Organically Combined SO$_2$ | | 1.18 |
| Methoxyl | | 11.07 |
| Carbon (C) | | 50.50 |
| Hydrogen (H) | | 5.40 |
| Total Nitrogen (as NH$_3$) | | 0.32 |
| Sulfated Ash | | 18.70 |
| Na$_2$SO$_4$ | 93.5% of sulfated ash | |
| CaSO$_4$ | 3.46% of sulfated ash | |
| Cr$_2$O$_3$ | 0.25 of sulfated ash | |
| Fe$_2$O$_3$ | 0.023% of sulfated ash | |

Other lignosulfonic materials useful in the present invention can be prepared from commercial sulfite waste liquor by the procedure of Markham et al., J. Am. Chem. Soc. 71, 3599 (1949). Norlig[TM] and Marasperse[TM] are commercial lignosulfonates which can be used; typical analyses are as follows:

| Typical Analyses (Moisture-Free Basis) | | | |
|---|---|---|---|
| | Norlig[TM] | Marasperse[TM] CB | Marasperse[TM] N22 |
| pH--3% Solution | 4.4 | 8.5–9.0 | 7.0–7.5 |
| Total Sulfur as S, % | 5.40 | 2.60 | 5.30 |
| Sulfate Sulfur as S, % | 0.30 | 0.10 | 1.20 |
| Sulfite Sulfur as S, % | 0.05 | — | 0.06 |
| CaO, % | 6.34 | 0.03 | 0.63 |
| MgO, % | 0.37 | Trace | 0.95 |
| Na$_2$O, % | — | 9.90 | 10.00 |
| Fe$_2$O$_3$, % | 0.07 | 0.03 | 0.28 |
| Reducing Sugars, % | 18.50 | none | none |
| OCH$_3$, % | 8.20 | 12.7 | 11.20 |
| Physical Characteristics | | | |
| | Norlig[TM] | Marasperse[TM] CB | Marasperse[TM] N22 |
| Usual Form | Powder | Powder | Powder |
| Moisture Content (Max. % H$_2$O) | 4.5 | 7.0 | 6.0 |
| Color | Brown | Brown | Dark Brown |
| Bulk Density (lbs./cu.ft.) | 33–35 | 35–40 | 35–40 |
| Solubility in Water (%) | 100 | 100 | 100 |
| Solubility in Oils and Most Organic Solvents (%) | 0 | 0 | 0 |
| Surface Tension, 1% Sol'n (in dynes/cm) | — | 51.4 | 52.8 |

Another lignosulfonate useful in the present invention is a calcium lignosulfonate known as Lignosol BD[TM] of which typical analyses are as follows:

| Typical Analyses | |
|---|---|
| Moisture | 4% |
| Lime CaO | 7.0 |
| Reducing bodies | 20.0 |
| Sulfur | 5.0 |
| Iron (max.) | 0.05 |
| pH 50% Solution | 4.6 |
| Methoxyl | 7.6 |
| Sulfonate sulfur | 3.5 |
| Ash | 10.0 |

Coprecipitates of lignosulfonic acid and anti-inflammatory agents can also be prepared using potassium lignosulfonate, lithium lignosulfonate and magnesium lignosulfonate.

It has been found that coprecipitates of lignosulfonic acid and anti-inflammatory agents can readily be prepared from both high and low molecular weight fractions of ammonium and sodium lignosulfonates, said fractions having been prepared by osmotic partitioning. Methanol may also be used to obtain a highly suitable fraction of ammonium lignosulfonate, being low in iron and manganese, for preparing coprecipitates with anti-inflammatory agents.

It was further discovered that the lignosulfonates can be suitably refined using cation exchange resins to produce aqueous solutions of lignosulfonic acid containing only traces of minerals such as iron and manganese. The solutions of refined lignosulfonic acid may be used as such or can be reconverted to lignosulfonates to prepare the preferred novel coprecipitates of this invention. Removal of heavy metals increases the stability of the coprecipitates on long term storage.

Illustratively, a 30 wt./vol. % solution of ammonium Peritan is treated with cation exchange resins such as Amberlite 252™ and Amberlite IRP-69™ (Rohm & Haas) to reduce the concentration of iron and manganese to very low levels.

The therapeutic efficacy of the coprecipitate is maintained when the amount of the lignosulfonic acid present in the coprecipitate varies from 3.0 to 10.0 weight % and the amount of the anti-inflammatory agents aspirin, phenylbutazone or indomethacin in the coprecipitate varies from 90.0 to 97.0 weight %.

Below about 4% lignosulfonic acid content, the coprecipitates are less effective in preventing irritation of the gastric mucosa. Aspirin-lignosulfonic acid coprecipitates having a lignosulfonic acid content above about 6% are less stable on prolonged storage due to breakdown of the aspirin to salicylic acid. Therefore, coprecipitates containing from about 4 to about 6 weight % lingosulfonic acid and from about 94 to about 96 weight % of the anti-inflammatory agents aspirin, phenylbutazone or indomethacin are preferred.

A general procedure for preparing the novel coprecipitates of the present invention is as follows.

An aqueous solution of a lignosulfonate is prepared and filtered to remove insoluble material. A solution of an anti-inflammatory agent as, for example, aspirin, in a dilute aqueous basic solution is prepared and the two solutions are combined with stirring. The stirred homogenous solution is acidified with a dilute mineral or organic acid, illustratively hydrochloric acid, sulfuric acid, glacial acetic acid and citric acid and the coprecipitate which is formed on adiculation is collected, washed with water and dried.

The free lignosulfonic acid may also be used to form the coprecipitate and in addition may serve to acidify the basic solution of anti-inflammatory agent thus circumventing the need of other acids such as those illustrated above. The above procedure is carried out at a temperature of from about 0° C. to about 25° C., a temperature range of from about 0° C. to about 15° C. being preferred.

Alternate procedures for preparing the combined solution of lignosulfonates and anti-inflammatory agents prior to acidification will be readily recognizable to artisans or find exemplification in the examples. Illustratively, lignosulfonates in solid form rather than as an aqueous solution may be added to aqueous solutions of anti-inflammatory agents solubilized with a base. Removal of undissolved solids sometimes attendant to lignosulfonates may be accomplished by clarification methods other than filtration as, for example, by centrifugation, sedimentation and decantation or combinations of decantation with filtration or centrifugation. Further, clarification may be accomplished after combining lignosulfonates and the basic solution of anti-inflammatory agent.

The dried coprecipitate is assayed for the respective amounts of lignosulfonic acid and aspirin. The following factors are useful in adjusting the amount of lignosulfonic acid in the coprecipitate: (1) dilution raises lignosulfonic acid content, (2) increasing the ratio of lignosulfonic acid to anti-inflammatory agent increases lignosulfonic acid content, and (3) weakly acidic materials generally increase the lignosulfonic acid content of the coprecipitate as compared to stronger acids for a given ratio of anti-inflammatory agent to lignosulfonic acid. Inasmuch as (1) and (2) also decrease total yield, the importance of utilizing (3) can readily be realized.

The following examples illustrate the general method of preparation of the novel water insoluble coprecipitates of the present invention and the variations which can be employed. All of the water insoluble coprecipitates disclosed in the examples were prepared with the reaction mixture maintained in the preferred temperature range of 0° C. to 15° C. It is to be understood that the examples are merely illustrative and not to be construed as limiting.

EXAMPLE 1

A solution of 500 g. ammonium lignosulfonate in 1200 ml. water was filtered. The small amount of residue was washed with water, the filtrates were combined and water added to give a final volume of 1500 ml. A solution of 50 g. sodium carbonate and 125 g. of aspirin in one liter of water was added to the ammonium Peritan solution with stirring and the resulting solution was acidified with 500 ml. of 2N hydrochloric acid. The mixture was cooled and filtered and the coprecipitate washed with 500 ml. of dilute acetic acid followed by 200 ml. hexane. The coprecipitate was air dried at room temperature followed by drying at 50° C. The weight of the coprecipitate was 63 g. The dried coprecipitate was assayed and contained (by weight) 89% aspirin and 9.8% lignosulfonate.

EXAMPLE 2

A stirred solution of 50 g. of sodium lignosulfonate in 250 ml. water was treated with a solution of 10 g. sodium carbonate and 25 g. aspirin in 200 ml. of water. The stirred mixture was acidified with 100 ml. of 2N hydrochloric acid, cooled to about 10° C. and filtered. The coprecipitate was washed with distilled water until the filtrate became clear and then was washed with 200 ml. of hexane. The air dried product weighed 12 g. The coprecipitate was assayed and contained (by weight) 91% aspirin and 9% lignosulfonate.

EXAMPLE 3

A stirred solution of 125 g. of sodium citrate hydrate in 250 ml. of water was treated with 25 g. of aspirin. Sodium Peritan (25 g.) was added and the mixture was stirred until solution of the solids was effected. The solution was filtered and the filtrate acidified with approximately 600 ml. of 2N hydrochloride acid. The coprecipitate was filtered and washed with water until the filtrate became clear and then washed with 200 ml. of n-hexane. The product weighed 17.5 g. after air drying. The coprecipitate was assayed and contained (by weight) 90% aspirin and 8.5% lignosulfonate.

EXAMPLE 4

A solution of 1000 g. of ammonium lignosulfonate in 2.5 liters of distilled water was filtered through No. 1 Whatman paper. A solution of 200 g. of sodium bicarbonate and 250 g. of aspirin in 2.5 liters of distilled water was added and the resulting solution was stirred for about five minutes. Eighty ml. of conc. sulfuric acid was added which brought the pH of the solution to 1.0. The coprecipitate was collected on a medium porosity canvas filter and washed three times with distilled water. The product was dried in a fluid-bed dryer without heat for one hour and then for 10 minutes at 40°–50° C. The dried coprecipitate weighed 165 g. The coprecipitate was assayed and contained (by weight) 90% aspirin and 8.5% lignosulfonate.

EXAMPLE 5

To a stirred solution of 30 g. sodium carbonate and 100 g. of aspirin in two liters of water was added 200 g. dry ammonium lignosulfonate. When the solids had dissolved, the solution was acidified with 180 ml. of 2N sulfuric acid. The coprecipitate was collected and washed with water. The coprecipitate was suspended in one liter of a buffer solution, pH of 2.6 (potassium acid phthalate in hydrochloric acid) and the suspension was spray dried at 230°–250° C. The coprecipitate was assayed and contained (by weight) 89% aspirin and 5.7% lignosulfonate.

EXAMPLE 6

A mixture of 800 g. of ammonium lignosulfonate and four liters of methanol was stirred for 15 minutes, the methanol insoluble material was allowed to settle and the clear supernatant was decanted and evaporated in a film coating apparatus. The dried solid material was redissolved in four liters of methanol, the mixture was filtered through No. 1 Whatman paper and the methanol filtrate evaporated. A solution of 200 g. of the methanol soluble lignosulfonate in one liter of water was added to a solution of 100 g. of aspirin and 30 g. sodium carbonate in two liters of water. The mixture was acidified with 180 ml. of 2N sulfuric acid and the coprecipitate collected and washed with water. The coprecipitate was dried at room temperature overnight and weighed 65 g.

EXAMPLE 7

A mixture of 400 g. of ammonium lignosulfonate in two liters of methanol was stirred for 15 minutes, the insoluble material was allowed to settle and the supernatant liquid was filtered through No. 1 filter paper. The methanol filtrate was evaporated to dryness and 100 g. of the dried solid was dissolved in 400 ml. of water. The aqueous solution was passed through a cation exchange resin followed by 300 ml. of wash water. The solution was added to a solution of 50 g. of aspirin and 14.8 g. of sodium carbonate in one liter of water. Fifty ml. of 2N sulfuric acid was added which reduced the pH of the aqueous solution from 3.0 to 2.1. The coprecipitate was filtered, washed with water and air dried overnight. The coprecipitate weighed 24 gm. It was assayed and contained (by weight) 96% aspirin and 2.9% lignosulfonate.

EXAMPLE 8

Two hundred grams of methanol soluble ammonium lignosulfonate was dissolved in 700 ml. of water and the solution was passed through a column of cation exchange resin IRP-69. After water washing the column with water, the volume of total effluent was made up to one liter. A solution of 29.6 g. of sodium carbonate and 100 g. of aspirin in two liters of water was mixed with the deionized lignosulfonic acid solution and the mixture acidified with 280 ml. of 2N sulfuric acid. The coprecipitate was collected on a filter and washed with water. The coprecipitate was suspended in one liter of distilled water and the mixture spray dried at 160°–165° C. The dried coprecipitate weighed 65.0 g. It was assayed and contained (by weight) 94% aspirin and 4.6% lignosulfonate.

EXAMPLE 9

A 30% aqueous solution of ammonium lignosulfonate was deionized by passing it over ion exchange resin IR-252 Amberlite™ in a column. After washing the column with water and combining all effluent, the overall concentration of lignosulfonic acid was 20 weight %. Ammonium hydroxide (28% ammonia) was added to adjust the pH to 4.5 and the solution was spray dried in a Nichol Nerdo-Niro spray drier (Nichols Engineering & Research Corporation, New York City, New York, with the following settings: atomizer 4, inlet temperature 160°–165° C., outlet temperature 65°–70° C. Analyses showed the iron and manganese content of the spray dried ammonium lignosulfonate to be 1.5 ppm. and 3.5 ppm. respectively on a dry basis. To a cold (5° C.) solution of 750 g. of the spray dried ammonium lignosulfonate in 28 liters of distilled water was added with stirring a cold solution (5° C.) of 519 g. sodium carbonate monohydrate and 1,500 g. aspirin in 15 l. of water. To the final cold solution surrounded by an ice bath was added with stirring 3 l. of glacial acetic acid in portions. After the first 1200 ml. portion of glacial acetic acid was added, the mixture was stirred for one hour. The remaining glacial acetic acid was added in 300 ml. portions at 15 minute intervals. After the last portion was added, the mixture was allowed to stir for one hour. The coprecipitate was separated by filtration, washed with 1.2 l. of glycine buffer solution and air dried. The product coprecipitate weighed 946 g. The coprecipitate analyzed 94% aspirin, 4.4% lignosulfonic acid and 0.1% salicylic acid. After storage at room temperature for 152 days the coprecipitate analyzed 0.24% salicylic acid.

EXAMPLE 10

The procedure of Example 9 for preparing the coprecipitate was repeated using ammonium lignosulfonate which had not been deionized except that the glacial acetic acid remaining after the first 1200 ml. addition, i.e., 1800 ml. was pumped in at the rate of 20 ml./minute. Weight of air dried product was 1025 g. lignosulfonic acid content was found to be 4.95 weight %.

EXAMPLE 11

One hundred grams of lignosulfonic acid in one liter volume of aqueous solution obtained from ion exchange resin (IR 252) treatment of ammonium lignosulfonate was added with stirring to a solution of 14.8 g. anhydrous sodium carbonate and 80 g. aspirin in 2 liters distilled water at 10° C. Stirring was continued while cooling in an ice bath for 1.5 hr. during which time coprecipitate slowly formed. Initial pH after mixing the two solutions was 3.1 and the pH gradually increased to 3.8. After filtration and washing with phthalalte buffer (pH 2.5 ) and air drying, the product weighed 10 g. Lignosulfonic acid was found by analysis to be 4.62 and salicylic acid content was 0.09%.

EXAMPLE 12

A solution of 7.8 g. of sodium carbonate in 500 ml. water was cooled to 8° C. and 25 g. of aspirin was added. A cold solution of 50 g. of Lignosol BD™ (calcium lignosulfonate) in 250 ml. of water and 70 ml. of 2.0 N sulfuric acid was added to the first solution, and the resulting coprecipitate was collected on a Buchner funnel and washed with cold distilled water. The product was dried by lyophillization at a temperature of 93° C. for 25 minutes, then by continued lyophillization for 20 hours at room temperature. The product weighed 14.7 g. and assayed 8.27% lignosulfonate, 1.25% mositure and 0.069% salicylic acid.

EXAMPLE 13

A stock solution of 14.8 g. of sodium carbonate and 50 g. of aspirin in 900 ml. of water was prepared and cooled to slightly below 8° C. Eight separate mixtures were prepared below 8° C. with stirring, using 100 ml. of the foregoing solution in each, varying amounts of methanol soluble ammonium lignosulfonate 20% solution in water and 14 ml. of 2N sulfuric acid. The coprecipitate from each mixture was collected on a filter, washed and dried at room temperature and assayed for the amount of lignosulfonate present in the coprecipitate. The data is summarized as follows:

| Mixture | Wt. of Aspirin in gms. | Wt. of Ammonium Peritan in gms. | % Lignosulfonate in Coprecipitate |
|---|---|---|---|
| 1 | 5 | 1.0 | 2.43 |
| 2 | 5 | 1.25 | 2.63 |
| 3 | 5 | 2.5 | 3.46 |
| 4 | 5 | 5.0 | 4.23 |
| 5 | 5 | 7.5 | 4.54 |
| 6 | 5 | 10.0 | 4.57 |
| 7 | 5 | 12.5 | 4.57 |
| 8 | 5 | 15.0 | 4.61 |

EXAMPLE 14

To a stirred solution of 5 g. of phenylbutazone in 300 ml. of water was added 3 g. of sodium carbonate and 2.5 g. of ammonium lignosulfonate. Stirring was continued for 15 minutes after which 20 ml. of 2N sulfuric acid was added slowly. The mixture was allowed to stand one hour to allow carbon dioxide gas to escape. The coprecipitate was collected on a Buchner funnel and washed twice with water and allowed to dry overnight at room temperature.

EXAMPLE 15

A solution of 5 g. of sodium hydroxide in 200 ml. of distilled water was prepared and 10 g. of phenylbutazone was dissolved in the dilute basic solution. Ten gms. of ammonium lignosulfonate was added slowly to the stirred solution after which the solution was cooled in a refrigerator. After cooling to about 15° C., 30 ml. of 18% hydrochloric acid was added to form the coprecipitate. The mixture was allowed to stand overnight after which it was filtered and the product was washed with distilled water and dried in an oven at 50° C. The yield of coprecipitate was 5.0 g. and contained (by weight) 93% phenylbutazone and 7.0% lignosulfonic acid.

EXAMPLE 16

One gram of indomethacin in 80 ml. of water was mixed with 15 ml. of 5% sodium hydroxide solution. To the stirred solution was added 2.0 g. of sodium lignosulfonate. After five minutes stirring to give a clean solution, 20 ml. of 2.0 N sulfuric acid was added slowly to form the coprecipitate. After standing at room temperature overnight, the coprecipitate was collected and dried.

ANALYTICAL METHODS

Spectrophotometric Analysis for Lignosulfonic Acid in Anti-Inflammatory Coprecipitates The lignosulfonic acid content of the coprecipitate is determined by the following method.

Weigh accurately about 100 mg. of sample into a small beaker and add 10–15 ml. of chloroform. Swirl or stir for five minutes to dissolve away the aspirin and collect insoluble material on No. 3 fluted Whatman filter paper which has been wetted with chloroform. Wash insolubles from the beaker onto the filter paper with chloroform and continue washing the filter paper into the filtrate with five 10 ml. portions of chloroform. Discard all filtrate. Allow the chloroform to evaporate from the filter paper and rinse the lignosulfonic acid from the paper with water into a 100 ml. volumetric flask. Continue rinsing until no yellow coloration remains in the rinse from the paper. Dilute the filtrate to volume with water. Balance the Cary spectro-photometer at 282 nanometers (nm) with water. Record absorbance of sample at 282 nm. Calculate lignosulfonate or lignosulfonic acid content as follows:

$$\% \text{ lignosulfonic acid} = \frac{(756)\ (Au^* \ 282\ nm)}{\text{weight of sample in mg}}.$$

*$Au$ is absorbance of sample at specified wave length.

Spectrophotometric Analysis for Acetylsalicylic Acid and Salicylic Acid

Weight accurately 150.0 ± 0.1 mg. of sample directly into a 50 cc. beaker. Add 40 cc. chloroform to the beaker and stir for 5 minutes. Filter on No. 3 Whatman filter paper into a 200 cc. volumetric flask. Rinse the filter paper with chloroform rinse from the beaker. Discard the filter paper. Dilute the filtrate to volume with chloroform. Place a 10 ml. aliquot in a 100 cc. volumetric flask and dilute the volume with water. Balance the Cary spectrophotometer at 282 nm. with water using cells 1 cm. thickness. Record the absorbance at 278 nm. and 308 nm. Calculate as follows:

$$\% \text{ acetylsalicylic acid} = \frac{[Au\ 278\ nm. - Au\ 308\ nm.(0.1959)] \times 10^4}{0.3650 \times 150}$$

$$\% \text{ salicylic acid} = \frac{33.33 \times Au\ 308\ nm.}{0.730}$$

Gas chromatographic

Analysis for Phenylbutazone: Phenylbutazone is analyzed by gas chromatographic procedure from a chloroform solution using tribenzylamine as the internal standard for quantitation by the relative peak height technique.

Formulation and Administration

The novel anti-inflammatory compositions of this invention can be formulated readily into pressed or coated tablets, encapsulated or other pharmaceutical dosage forms. Any of the various adjuvant materials ordinarily found in conventional pharmaceutical tablets of the art can be employed in preparing such tablets. These adjuvants include, for example, fillers such as cornstarch, lactose, demoisturizers, and dicalcium phosphate. They may also include disintegrating agents such as maize starch, lubricants such as talk, calcium stearate, etc. The methods and techniques which will be most suitable in formulating the present compositions into such tablets will be readily apparent to those skilled in the art.

Typical oral dosages of the compositions of this invention will vary within rather wide limits. For example, in the case of a tablet containing 340 mg. of an aspirin-lignosulfonic acid coprecipitate, a typical oral dosage for an adult will be up to two tablets every four hours as required. In the case of a tablet containing about 680 mg. of said coprecipitate of aspirin and lignosulfonic acid, a typical oral dosage for an adult will be up to one tablet every four hours as required. In the case of children age 6 to 12 years, or in the case of debilitated patients, smaller doses may, of course, be more appropriate. On the other hand, in the case of patients experiencing more severe discomfort due to pain, more frequent administration of the preparations may be prescribed. It should be fully understood, therefore, that the typical dosages mentioned herein are exemplary only and that they do not to any extent limit the scope or the practice of the present invention.

Pharmacology

The coprecipitates prepared as described in the foregoing examples were mixed with 10% disintegrating corn starch and the mixtures were applied to an area of 5 $cm^2$ of gastric mucosa of anesthetized cats and allowed to remain without drainage of fluids from the area for a prescribed length of time. Controls using aspirin and starch were also applied to an equal area of the gastric mucosa of the same cat. The tissue in each case was examined macroscopically and microscopically for bleeding, erosion and ulceration.

The coprecipitates prepared in Examples 1 to 5 were compared in situ against aspirin and the results are summarized in Table I and show that the coprecipitates impart a high degree of protection.

Table II shows the composite effect of the coprecipitates by number of animals exhibiting any bleeding, erosions and ulceration as compared to aspirin.

The coprecipitate of Example 9 was found to be highly effective in reducing bleeding due to aspirin applied to the gastric mucosa of anesthetized cats. The coprecipitate when applied in the amount of 10 mg. contained aspirin per 5 $cm^2$ area reduced bleeding compared to aspirin alone, as determined in four cats after 30 minutes of continuous application without drainage from the area, by 88.6%. The results ae statistically significant at the 99.5% level.

In summary, the present invention involves the use of water insoluble coprecipitates of lignosulfonic acids and anti-inflammatory agents such as aspirin, phenylbutazone and indomethacin. The water insoluble coprecipitates retain the valuable anti-inflammatory properties of the anti-inflammatory moieties of aspirin, phenylbutazone and indomethacin and they are effective in reducing or preventing gastric irritation such as bleeding and ulceration.

The water insoluble coprecipitates contain 3–10 weight % lignosulfonic acid, preferably 4–6 weight %, and 90–97 weight % anti-inflammatory agent, preferably 94–96 weight %.

TABLE I

TOPICAL EFFECTS OF ASPIRIN AND COPRECIPITATE ON THE STOMACH MUCOSA OF CATS IN SITU

| No. of Cats | Example No. | Quantity, mg. Per 5 $cm^2$ | Average Exposure Time, min. | Ulcer Index (a) | Percent Protection | Percent Reduction in Bleeding |
|---|---|---|---|---|---|---|
| 4 | Aspirin | 36 | 35 | 62 | | |
|   | Ex. 1 | 36 | 35 | 45 | 28 | 100 |
| 5 | Aspirin | 10 | 70 | 70 | | |
|   | Ex. 1 | 10 | 70 | 20 | 72 | 83 |
| 4 | Aspirin | 36 | 56 | 57 | | |
|   | Ex. 2 & 3 | 36 | 56 | 11 | 81 | 72 |
| 10 | Aspirin | 320 | 150 | 82 | | |
|    | Ex. 4 | 320 | 150 | 43 | 48 | 82 |
| 4 | Aspirin | 10 | 45 | 53 | | |
|   | Ex. 5 | 10 | 45 | 22 | 59 | 54 |

(a) Ulcer Index: Maximum score possible under system is 160. Hemmorhage maximum (dark bleeding sites under mucosa). Max. 40 Erosions (sloughing of tissue) Max. 40 Ulceration (deep penetration through mucosa) Max. 80

TABLE II

TOPICAL EFFECTS OF ASPIRIN AND COPRECIPITATES ON CAT GASTRIC MUCOSA IN SITU
(Composite of Results with Material from Examples 1–5)

| Cpd. | No. Cats | Quantity mg/5 $cm^2$ | Average Exposure Time (min.) | Bleeding(a) | Erosions | Ulceration(a) |
|---|---|---|---|---|---|---|
| Aspirin | 18 | 10 | 65 | 17/18 | 18/18 | 1/18 |
| Coprecipitate | 15 | 10 | 65 | 11/15 | 5/15 | 0/15 |
| Aspirin | 8 | 36 | 45 | 6/8 | 5/8 | 5/8 |
| Coprecipitate | 8 | 36 | 45 | 2/8 | 3/8 | 1/8 |
| Aspirin | 9 | 320 | 150 | 5/9 | 7/9 | 6/9 |
| Coprecipitate | 9 | 320 | 150 | 2/9 | 7/9 | 4/9 |
| | | | Total aspirin | 28/35 | 30/35 | 12/35 |

TABLE II-continued

TOPICAL EFFECTS OF ASPIRIN AND COPRECIPITATES ON CAT GASTRIC MUCOSA IN SITU
(Composite of Results with Material from Examples 1–5)

| Cpd. | No. Cats | Quantity | Average Exposure Time (min.) | Bleeding(a) | Erosions | Ulceration(a) |
|---|---|---|---|---|---|---|
| Total Coprecipitates | | | | 15/32 | 15/32 | 5/32 |

(a) Ratio of cats exhibiting effects to number tested.

The phenylbutazone lignosulfonic acid coprecipitates of Example 15 were evaluated in the same manner on the gastric mucosa of anesthetized cats comparing it with phenylbutazone and starch. Ten per cent starch was mixed with each agent. In one test 10 mg. of each were applied to separate 5 cm² mucosa areas of one cat for 85 minutes after which time the mucosa was examined both macroscopically and microscopically. Results were as follows:

| Aspirin | Phenylbutazone | Coprecipitate of Example 15 |
|---|---|---|
| Excess bleeding. Much tissue erosion. Considerable denuding of mucosa. | Some bleeding. Few tissue erosions. Some denuding of tissue. | Tissues were essentially normal. |

In another test on the gastric mucosa of one cat, 10 mg. of phenylbutazone were applied to each of two areas and 10 mg. of the coprecipitate of lignosulfonic acid-phenylbutazone applied to another. Observations after four hours exposure time were as follows:

| Phenylbutazone I | Phenylbutazone II | Coprecipitate of Example 15 |
|---|---|---|
| Four bleeding sites. | One small bleeding site. | No bleeding sites, mucosa normal. |

In additional tests on mucosa of cats, using two phenylbutazone controls all at the rate of 10 mg./5 cm², the following observations were made.

| Length of Exposure Min. | I Phenylbutazone | II Phenylbutazone | Coprecipitate of Example 15 |
|---|---|---|---|
| 60 | Several blistered areas. | Several blistered areas. | Tissue essentially by normal. |
| 240 | Four bleeding sites. | One bleeding site. | No bleeding, mucosa normal. |

We claim:

1. A water insoluble anti-inflammatory coprecipitate of a lignosulfonic acid and an anti-inflammatory agent selected from the group consisting of aspirin, phenylbutazone and indomethacin wherein the amount of said lignosulfonic acid in the coprecipitate varies from 3 to 10 weight % and the amount of anti-inflammatory agent in the coprecipitate varies from 90–97 weight %, said coprecipitate formed by acidifying an aqueous solution of said lignosulfonic acid and the anti-inflammatory agent, said aqueous solution being substantially free of undissolved solids prior to acidification and said solution formed by mixing said lignosulfonic acid or an aqueous solution thereof and an aqueous solution formed by solubilizing said anti-inflammatory agent with a base.

2. A water insoluble anti-inflammatory coprecipitate of a lignosulfonic acid and an anti-inflammatory agent selected from the group consisting of aspirin, phenylbutazone and indomethacin wherein the amount of said lignosulfonic acid in the coprecipitate varies from 3 to 10 weight % and the amount of the anti-inflammatory agent in the coprecipitate varies from 90–97 weight %, said coprecipitate formed by acidifying a basic solution at 0° to 25° C., said solution formed by mixing a filtered aqueous solution of said lignosulfonic acid and a dilute aqueous basic solution of the anti-inflammatory agent.

3. A water insoluble anti-inflammatory coprecipitate of a lignosulfonic acid and an anti-inflammatory agent selected from the group consisting of aspirin, phenylbutazone and indomethacin wherein the amount of said lignosulfonic acid in the coprecipitate varies from 4 to 6 weight % and the amount of the anti-inflammatory agent in he coprecipitate varies from 94–96 weight %, said coprecipitate formed by acidifying a basic solution at 0° to 25° C., said solution formed by mixing a filtered aqueous solution of said lignosulfonic acid and a dilute aqueous basic solution of the anti-inflammatory agent.

4. The water insoluble coprecipitate of claim 3 wherein the anti-inflammatory agent is aspirin.

5. The water insoluble coprecipitate of claim 1 wherein the anti-inflammatory agent is phenylbutazone.

6. The water insoluble coprecipitate of claim 1 wherein the anti-inflammatory agent is indomethacin.

7. The water insoluble coprecipitate of claim 1 comprising methanol soluble lignosulfonic acid and aspirin.

8. The water insoluble coprecipitate of claim 7 wherein the lignosulfonic acid in the coprecipitate is 4–6 weight %.

9. A water insoluble coprecipitate of claim 1 comprising cation-exchanged refined lignosulfonic acid and aspirin.

10. The water insoluble coprecipitate of claim 9 wherein the lignosulfonic acid in the coprecipitate is 4–6 weight %.

11. A method of treating inflammation in warm-blooded animals which comprises administering to said warm-blooded animals, for its anti-inflammatory effect, an effective amount of a water insoluble coprecipitate wherein said coprecipitate comprises said lignosulfonic acid and an anti-inflammatory agent selected from the group consisting of aspirin, phenylbutazone and indomethacin in accordance with claim 1.

12. The process according to claim 11 wherein the amount of lignosulfonic acid present in the water insoluble coprecipitate varies from 4 to 6 weight % and the amount of the anti-inflammatory agent varies from 94–96 weight %.

13. The process according to claim 12 wherein the anti-inflammatory agent is aspirin.

14. The process according to claim 12 wherein the lignosulfonic acid is methanol soluble lignosulfonic acid.

15. The process according to claim 12 wherein the lignosulfonic acid is cation-exchanged refined lignosulfonic acid.

16. A composition useful for its anti-inflammatory effect comprising (A) an effective amount of 340 milligrams of an anti-inflammatory water insoluble coprecipitate in accordance with claim 1, and (B) a pharmaceutically acceptable carrier therefor.

17. The composition of claim 16 wherein the anti-inflammatory water insoluble coprecipitate contains 4 to 6 weight % lignosulfonic acid and 94 to 96 weight % anti-inflammatory agent.

18. The composition of claim 17 wherein the lignofulfonic acid is methanol soluble lignosulfonic acid.

19. The composition of claim 18 wherein the lignosulfonic acid is cation-exchanged refined lignosulfonic acid.

* * * * *